(12) United States Patent
Goetz

(10) Patent No.: US 9,633,170 B2
(45) Date of Patent: Apr. 25, 2017

(54) REMOTELY-REQUESTED INTEGRITY DIAGNOSTICS

(75) Inventor: Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 1196 days.

(21) Appl. No.: 12/738,056

(22) PCT Filed: Sep. 29, 2008

(86) PCT No.: PCT/US2008/078127
§ 371 (c)(1),
(2), (4) Date: Apr. 14, 2010

(87) PCT Pub. No.: WO2009/055206
PCT Pub. Date: Apr. 30, 2009

(65) Prior Publication Data
US 2010/0222846 A1    Sep. 2, 2010

Related U.S. Application Data

(60) Provisional application No. 61/000,161, filed on Oct. 24, 2007.

(51) Int. Cl.
*A61N 1/08* (2006.01)
*A61N 1/37* (2006.01)
*G06F 19/00* (2011.01)

(52) U.S. Cl.
CPC ...... *G06F 19/3418* (2013.01); *G06F 19/3406* (2013.01); *A61N 2001/083* (2013.01)

(58) Field of Classification Search
CPC ............ A61N 2001/083; A61N 1/3708; G06F 19/3418
(Continued)

(56) References Cited

U.S. PATENT DOCUMENTS 6,044,297 A    3/2000  Sheldon et al.
6,442,432 B2 *  8/2002  Lee .................................. 607/59
(Continued)

FOREIGN PATENT DOCUMENTS

EP    1491234    12/2004
WO    WO96/22125    7/1996
(Continued)

OTHER PUBLICATIONS

PCT/US08/78134: Search Report and Written Opinion dated Jun. 9, 2009.
(Continued)

*Primary Examiner* — William Levicky
(74) *Attorney, Agent, or Firm* — Shumaker & Sieffert, P.A.

(57) ABSTRACT

In general, the invention is directed toward techniques for remotely monitoring the integrity of a medical device and its components. A remote networking device communicates with a medical device, e.g., an implantable medical device, via a network. The remote networking device sends a request for an integrity measurement to the medical device via the network, a remote network that requests a medical device to perform an integrity measurement. In response to the request, the medical device performs the requested integrity measurement. The medical device may transmit a result of the integrity measurement, e.g., a measured value, back to the remote networking device via the network.

22 Claims, 6 Drawing Sheets

(58) Field of Classification Search
  USPC .................................................... 607/60, 59
  See application file for complete search history.

(56) References Cited

U.S. PATENT DOCUMENTS

| | | | |
|---|---|---|---|
| 6,662,052 | B1 | 12/2003 | Sarwal et al. |
| 7,567,840 | B2 * | 7/2009 | Armstrong ...................... 607/27 |
| 7,988,728 | B2 * | 8/2011 | Ayre ............................. 623/3.28 |
| 2001/0031997 | A1 | 10/2001 | Lee |
| 2002/0029002 | A1 | 3/2002 | Bardy |
| 2002/0143372 | A1 | 10/2002 | Snell et al. |
| 2002/0183693 | A1 * | 12/2002 | Peterson et al. .............. 604/151 |
| 2004/0030358 | A1 * | 2/2004 | Rueter et al. ................... 607/27 |
| 2006/0089592 | A1 | 4/2006 | Kadhiresan et al. |
| 2006/0235289 | A1 | 10/2006 | Wesselink |
| 2007/0142868 | A1 | 6/2007 | Moon et al. |
| 2009/0138061 | A1 * | 5/2009 | Stephens et al. ............... 607/41 |

FOREIGN PATENT DOCUMENTS

| | | |
|---|---|---|
| WO | WO2004/067083 | 8/2004 |
| WO | WO2004/093989 | 11/2004 |
| WO | WO2006/099035 | 9/2006 |
| WO | WO2007/079543 | 7/2007 |
| WO | WO2007/112092 | 10/2007 |
| WO | WO2009/055202 | 4/2009 |
| WO | WO2009/055204 | 4/2009 |
| WO | WO2009/055205 | 4/2009 |
| WO | WO2009/055206 | 4/2009 |
| WO | WO2009/055207 | 4/2009 |

OTHER PUBLICATIONS

PCT/US08/78134: Response to Written Opinion filed Sep. 9, 2009.
PCT/US08/78134: 2$^{nd}$ Written Opinion dated Feb. 5, 2010.
PCT/US08/78134: Response to 2$^{nd}$ Written Opinion dated Apr. 5, 2010.
PCT/US08/78134: IPRP dated Apr. 22, 2010.
PCT/US08/78099: Search Report and Written Opinion dated Dec. 11, 2008.
PCT/US08/78099: Response to Written Opinion dated Aug. 14, 2009.
PCT/US08/78099: IPRP dated Feb. 2, 2010.
PCT/US08/78125: Search Report and Written Opinion dated Feb. 2, 2009.
PCT/US08/78114: Search Report and Written Opinion dated Feb. 10, 2009.
PCT/US08/78114: Response to Written Opinion dated Aug. 21, 2009.
PCT/US08/78114: IPRP dated Dec. 18, 2009.
PCT/US08/78127: Search Report and Written Opinion dated Dec. 12, 2008.
PCT/US08/78127: Response to Written Opinion dated Jun. 12, 2009.
PCT/US08/78127: IPRP dated Dec. 21, 2009.

* cited by examiner

REMOTELY-REQUESTED INTEGRITY DIAGNOSTICS

This application claims the benefit of and is a U.S. National Stage filing under 35 U.S.C. 371 of copending PCT Application Ser. No. PCT/US2008/078127, filed Sep. 29, 2008, which in turn claims the benefit of U.S. Provisional Application No. 61/000,161, filed Oct. 24, 2007, "Remotely-Requested Integrity Diagnostics, Stimulation," the disclosure of all of the above which is incorporated by reference herein in its entirety.

TECHNICAL FIELD

The invention relates to medical devices, and more particularly to integrity diagnostics for medical devices.

BACKGROUND

Medical devices may be used to treat a variety of medical conditions. Depending upon the medical condition, medical devices can be surgically implanted within, or connected externally to the patient receiving treatment. For some medical conditions, medical devices provide the best or only therapy to restore an individual to a more healthful condition and a fuller life. Examples of medical devices that deliver a therapy include electrical stimulators and therapeutic agent delivery devices.

If one or more components of a medical device are damaged or otherwise fail to operate as intended, the medical device may deliver ineffective or otherwise inappropriate therapy to the patient. In some cases, if a malfunctioning device is mistaken for a therapy that is truly ineffective for the particular patient, a therapy might be unnecessarily discontinued or have corrective action postponed. To help detect issues with a medical device or its components, integrity diagnostics may be performed.

Medical devices that deliver electrical stimulation do so via electrodes located on, or implanted within the patient. The electrodes may be at a target location for receipt of the stimulation in order to provide the desired therapeutic effect. The medical device containing the stimulation generator may be at a different, more convenient location given its size or shape, e.g., outside of the patient, or implanted within the patient at a location capable of accommodating the medical device. The medical device may be coupled to the electrodes by one or more leads, each lead containing one or more conductors.

Some medical devices perform integrity diagnostics to test the condition one or more of the electrodes, leads, or stimulation generator. One example of such an integrity test is to check the impedance between pairs of electrodes. This lead integrity test can be performed on leads and electrodes to verify that the leads and electrodes are functioning properly, and are positioned correctly. During testing, the medical device delivers a signal having a known electrical characteristic, e.g., current or amplitude, between two or more electrodes. Another electrical characteristic of the signal may be measured, and the impedance may be computed between electrodes using known fundamental relationships. The measured impedance value can give a medical professional or other user information relating to whether the electrodes involved in the test, as well as the conductors that coupled to those electrodes, are operating properly.

Medical devices that deliver a drug or other therapeutic substance may do so via a catheter, or the like, that is at least partially implanted within the patient. The catheter conveys the therapeutic substance from a pump within the medical device to a target location within the patient. A partial or complete blockage of the catheter could prevent the therapeutic substance from reaching the delivery site in the patient or, in the case of a partial obstruction, could prevent an adequate supply of the therapeutic substance from reaching the delivery site in the patient. A leak (e.g., due to a tear or cut), small or large, can also prevent the therapeutic substance from reaching the delivery site in the patient. A leak can result in a double problem. In addition to the lack of therapeutic substance supplied to the delivery site of the patient, the therapeutic substance could be dispersed elsewhere in the body of the patient, which may create further issues.

Some medical devices perform integrity diagnostics to test the condition one or more of the catheters or pumps. As an example, a catheter integrity test may measure the flow or pressure within the lumen of a catheter to detect tears or occlusions in the catheter. An abnormal increase in pressure within a lumen of a catheter may indicate an occlusion. Whereas, a decrease in pressure may indicate a tear. A decrease in flow may indicate either a tear or an occlusion. The measured flow and/or pressure values can give a medical professional or other user information relating to whether the catheter involved in the test is properly delivering a therapeutic substances to a target therapy delivery site.

SUMMARY

In general, the invention is directed toward techniques for remotely monitoring the integrity of a medical device and its components. A remote networking device communicates with a medical device, e.g., an implantable medical device, via a network. The remote networking device sends a request for an integrity measurement to the medical device via the network. The request may be initiated by a user of the remote networking device, such as a clinician, or a technician for a manufacturer of the medical device. In response to the request, the medical device performs the requested integrity measurement. The medical device may transmit a result of the integrity measurement, e.g., a measured value, back to the remote networking device via the network.

Any of a variety of integrity measurements may be requested at the remote networking device, and responsively performed by the medical device. For example, a lead impedance test, in which the medical device tests one or more lead-borne electrodes in the manner discussed above, may be requested at the remote networking device. As another example, catheter flow or pressure tests may be requested at the remote networking device. Additionally, the integrity of components of a stimulation generator, such as capacitors or voltage or current regulation circuitry, or of a pump mechanism, such as a stalled rotor or stuck piston, may be tested by the medical device as directed by a remote networking device. The integrity of any hardware or software component of an implantable or external medical device may be tested in response to a request from a remote networking device according to the invention.

In one embodiment, the invention is directed to a method comprising receiving a request to perform an integrity measurement at a medical device from a remote networking device via a network, performing the integrity measurement at the medical device of at least one component within or coupled to the medical device in response to the request, and sending a result of the integrity measurement from the medical device to the remote networking device via the network.

In another embodiment, the invention is directed to a medical device comprising a communication module, and a processor that receives a request from a remote networking device via a network and the communication module to perform an integrity measurement of at least one component within or coupled to the medical device, performs the integrity measurement in response to the request, and sends a result of the integrity measurement device to the remote networking device via the network and the communication module.

In another embodiment, the invention is directed to a method comprising sending a request from a remote networking device via a network to a medical device to perform an integrity measurement, and receiving a result of the integrity measurement from the medical device via the network.

In another embodiment, the invention is directed to a remote networking device comprising a communication module, and a processor to send a request to perform an integrity measurement to a medical device via the communication module and a network, and receive the result of the integrity measurement from the medical device via the network.

In another embodiment, the invention is directed to a system comprising a medical device, and a remote networking device that sends a request to perform an integrity measurement to the medical device via a network, wherein the medical device performs the integrity measurement and sends a result of the integrity measurement to the remote networking device via the network.

Embodiments of the invention may provide one or more advantages. For example, in some cases, a medical device does not perform integrity diagnostics unless requested by a clinician or other user using, for example, a medical device programmer. In such cases, the ability to remotely request integrity diagnostics may allow the condition of the medical device to be assessed without requiring a costly and time consuming clinic visit.

Furthermore, in situations in which the medical device does automatically and periodically perform an integrity measurement, such measurements may not be occurring at a necessary time to detect an intermittent integrity issue with a particular component. For example, some lead fractures occur only intermittently, e.g., when a patient is within a particular posture or activity state. The causes of intermittent integrity problems may even be difficult to replicate during a clinic visit. In such cases, an integrity measurement may be remotely requested to occur at a time in which an intermittent integrity problem is likely to be detectable by an integrity measurement, e.g., when a patient is at home assuming the problematic postures or activities.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
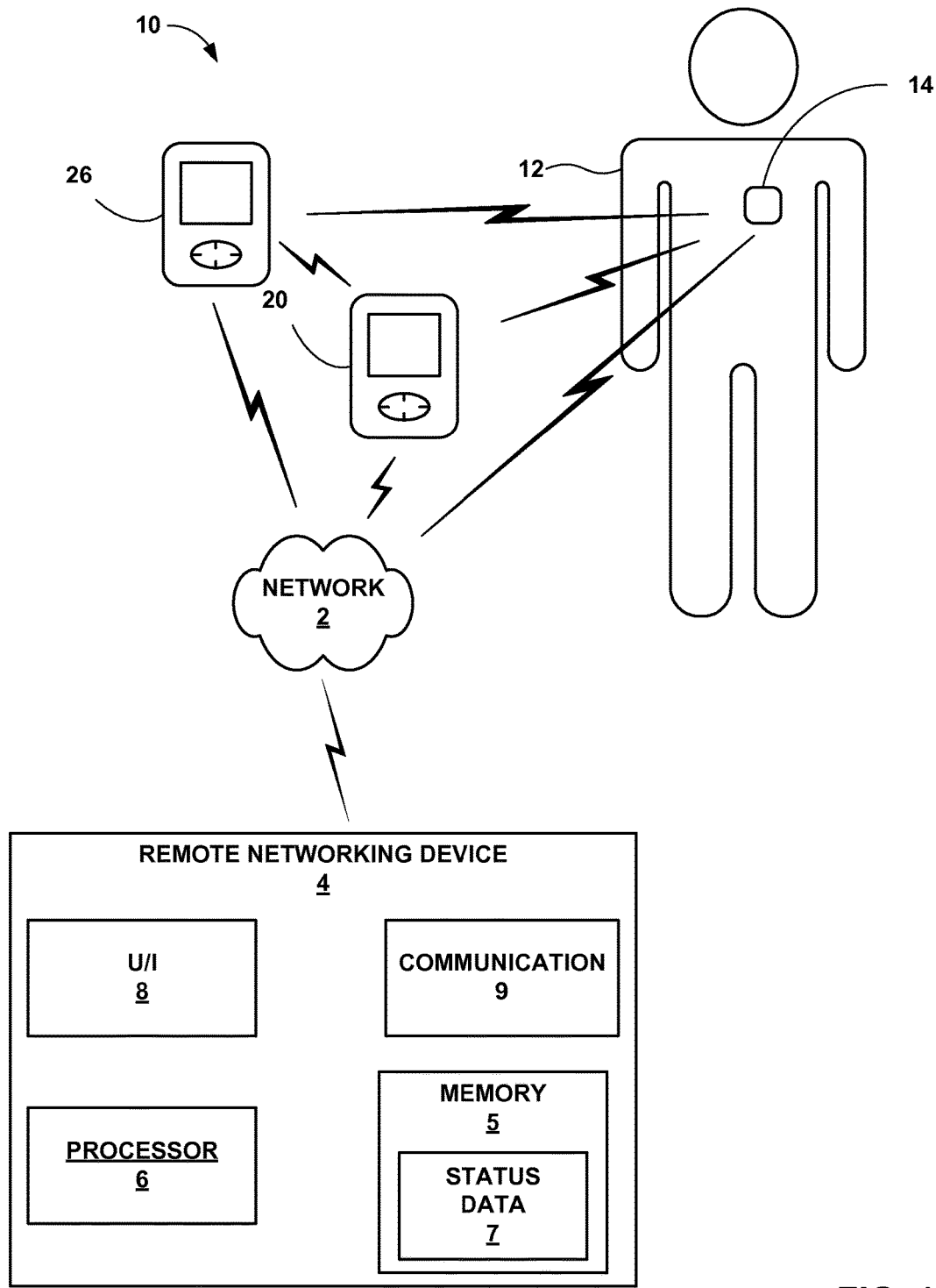
FIG. 1 is a conceptual diagram illustrating an example system in which integrity diagnostics may be remotely requested.

FIG. 1 is a conceptual diagram illustrating an example system 10 in which integrity diagnostics may be remotely requested. System 10 includes an implantable medical device (IMD) 14 implanted within patient 12, a clinician programmer 20, a patient programmer 26, and a remote networking device 4. As will be described in greater detail below remote networking device 4 sends integrity measurement requests to IMD 14 via network 2, and receives status data 7 from IMD 14 via the network in response to the requests. IMD 14 may communicate with network 2 directly or indirectly, e.g., via patient programmer 26. Although described herein with reference to IMDs 14, the invention is not limited to embodiments in which the medical device that performs remotely requested integrity measurements is implanted.

IMD 14 may deliver electrical stimulation therapy, drug therapy, or both to patient 12. Accordingly, IMD 14 may be an implantable pulse generator that delivers electrical stimulation therapy to patient 12 in the form of electrical pulses or substantially continuous time signals, a therapeutic agent delivery device that delivers a drug or other agent to patient 12, or a device or devices that deliver both electrical stimulation therapy and a therapeutic agent to patient 12. Although described herein with reference to medical devices that deliver a therapy to a patient, the invention is not so limited. For example, in some embodiments, a medical device may include sensors and act as a patient monitor without delivering therapy.

IMD 14 may deliver therapy according to one or more programs. Each program may include values for a number of therapy parameters, and the parameter values define the therapy delivered according to that program. In embodiments where IMD 14 delivers electrical stimulation therapy in the form of electrical pulses, the parameters may include voltage or current pulse amplitudes, pulse widths, as pulse rates, as well as combinations of electrodes selected for delivery of the stimulation and the polarities of the selected electrodes. In embodiments where IMD 14 includes a therapeutic agent delivery device instead of or in addition to an electrical stimulator, program parameters may define, as examples, flow rates, agent types or concentrations, and infusion types, e.g., continuous or bolus.

A clinician (not shown) may use clinician programmer 20 to specify one or more programs for the delivery of therapy by IMD 14. For example, the clinician may interact with a user interface of the programmer to select values for various therapy parameters. A number of programs specified in this manner may be tested by controlling the IMD to delivery therapy according to the programs, and desirable programs may be selected. Selected programs may be transmitted from clinician programmer 20 to one or both of IMD 14 and patient programmer 26 for long term storage and use.

Patient 12 may use patient programmer 26 to control the delivery of therapy by IMD 14. In particular, patient 12 may use patient programmer 26 to activate or deactivate therapy and select which from among a plurality of available programs stored within patient programmer 26 and/or IMD 14 will be used by IMD 14 to deliver therapy. Patient 12 may also adjust the therapy by, for example, adjusting the values of the parameters of the therapy programs. Further, in some embodiments, patient programmer 26 may send status data 8 from IMD 14 to remote networking device 4 via network 2.

IMD 14, clinician programmer 20, and patient programmer 26 may, as shown in FIG. 1, communicate with each other via local wireless communication. Clinician programmer 20 and patient programmer 26 may, for example, communicate via wireless communication with IMD 14 using RF telemetry techniques known in the art. For example, clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols. Clinician programmer 20 and patient programmer 26 need not communicate wirelessly, however. For example, clinician programmer 20 and patient programmer 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, e.g., utilizing network 2, which may comprise, for example, one or more of a local area network (LAN), wide area network (WAN), public switched telephone network (PSTN), or cellular telephone network.

As will be described in further detail below, IMD 14 may record integrity status data 7 during normal operation, i.e., during operation outside of a clinical environment. Remote networking device 4 may receive status data 7 from IMD 14 via network 2 and may present status data 7 to a user. Remote networking device 4 may also, in some example embodiments, analyze status data 7, and take action or suggest action to the user based on the analysis. The term "status data" in this disclosure refers to the status of system 10. Status data may include data that relates to data from one or more sensors, alerts from patient 12 and/or IMD 14, results of an integrity measurement, or any other data relevant to the status and operation of system 10.

In FIG. 1, IMD 14 communicates with remote networking device 4 via network 2, which may include one or more of a local area network (LAN), a wide area network (WAN), a landline telephone network, a cellular phone network, the Internet, and a wireless network. In particular, remote networking device 4 sends data to and receives data from IMD 14 over network 2. IMD 14 may connect directly to network 2 or may connect to network 2 via a link device, such as patient programmer 26, a wireless modem, a base station that provides, for example, recharge features and other features for patient programmer 26, a laptop or desktop computer, or other computing device with a connection to network 2.

IMD 14 may send data, such as status data 7, to remote networking device 4 on demand, according to a schedule, or on an opportunistic basis. IMD 14 may also transmit data to remote networking device 4 when its memory is full. In embodiments, in which IMD 14 communicates with network 2 via patient programmer 26, patient programmer 26 may temporary store and later transmit data to remote networking device 4, e.g., when the patient programmer's memory is full. In embodiments in which data is transmitted to remote networking device 4 on demand, patient 12 or a clinician may initiate the transmission of data to remote networking device 4. For example, patient 12 may interact with patient programmer 26 by pressing one or more buttons on a keypad or selecting an item from a display of a graphical user interface, to initiate data transmission to remote networking device 4. In another example, a clinician or other user at remote networking device 4 may interact with a user interface (U/I) 8 of remote networking device 4 to send a request to IMD 14 to retrieve status data 7. In this example, the clinician may be located at a clinic or other remote location relative to patient 12 and the request may be sent via network 2.

In an example in which data is transmitted to remote network device 4 according to a schedule, IMD 14 or patient programmer 26 may store a schedule in local memory and send data to remote network device 4 according to the schedule. Alternatively, remote networking device 4 may store a schedule in a memory 5, and a processor 6 of the remote networking device may send a request to IMD 14 (e.g., directly or indirectly via patient programmer 26) to retrieve data according to the schedule. In either case, the schedule specifies when data is sent to remote networking device 4. The schedule may specify that data is transmitted once per day, multiple times per day, once per week, multiple times per week, or at any other regular interval. The frequency at which data is transmitted may depend on the size of memory of IMD 14 and/or patient programmer 26 and the amount of data recorded by IMD 14.

In embodiments in which data is transmitted to remote networking device 4 on an opportunistic basis, IMD 14 and/or patient programmer 26 may transmit data over network 2 whenever they are within range of a link device that is connected to network 2. The link device may be a base station used for recharging patient programmer 26 that includes a connection to network 2, or any of the other link devices previously described in this disclosure.

It is also recognized that IMD 14 and/or patient programmer 26 may have substantially permanent connection to network 2, such as a wireless connection. In such cases, IMD 14 and/or patient programmer 26 may transmit data to remote networking device 4 in real-time. That is, IMD 14 and/or patient programmer 26 may transmit data to remote networking device 4 as data is generated.

Retrieving data from IMD 14 may also be performed through real-time interaction between patient 12 and a clinician. In this case, patient 12 and the clinician may communicate in real-time using patient programmer 26 and remote networking device 4, respectively. In this case, the clinician may send a request for data to IMD 14. In some embodiments, the request travels to IMD 14 via patient programmer 26. Patient programmer 26 may prompt patient 12 in response to receiving the request. For example, patient programmer 26 may display a message that requires confirmation from patient 12 before sending data to remote networking device 4.

A processor 6 of remote networking device 4 may analyze status data 7 relating to data from one or more sensors, alerts from patient 12 and/or IMD 14, or results of an integrity measurement. For example, status data 7 may include an alert from patient 12 that patient 12 is not receiving adequate therapy. Based on the alert, processor 6 may send a request to IMD 14 via network 2 to perform an integrity measurement, such as a lead integrity test on all electrodes, a lead integrity test on the electrodes currently being used to deliver therapy, a catheter integrity test, and/or a pump motor stall test.

As described previously, a lead integrity test may comprise measuring the impedance of an electrical path including an electrode, conductors that couple the electrode to an IMD, and tissue proximate to the electrode. Measuring the impedance of one or more electrical paths associated with one or more leads coupled to the IMD may aid in identifying dysfunctional electrical paths (e.g., paths that may be unable to provide adequate or reliable sensing or therapy due to, for example, degradation of the lead material, tissue growth proximate to an electrode, a short, or a fracture) among the paths provided by one or more leads coupled to the IMD. Copending U.S. Patent Publication No. 2006-0264777 by Touby A. Drew, entitled, "EVENT-BASED LEAD IMPEDANCE MONITORING" describes lead integrity tests in further detail.

Another example of an integrity measurement is a catheter integrity test. A pressure differential measurement in one or more catheters may be performed as an integrity measurement. Such a measurement may aid to detecting flow issues within the catheter. If functioning properly, the pressure within a catheter may be substantially constant. Thus, for a given flow rate the pressure within a catheter may be approximately equal to a normal, expected level. Deviations from the normal pressure may indicate failure of the catheter. A pressure measurement below the normal level may indicate that the catheter is ripped or leaking. A pressure measurement above the normal level may indicate that the catheter is occluded or kinked. In other embodiments, the flow of a therapeutic substance within one or more catheters may be measured to identify issues (e.g., occlusions, kinks, tears, and leaks) with the catheters. U.S. Pat. No. 7,320,676 by Keith A. Miesel, entitled, "PRESSURE SENSING IN IMPLANTABLE MEDICAL DEVICES", copending U.S. Patent Publication No. 2005-0245858 by Miesel et al., entitled, "BRANCHING CATHETER SYSTEMS WITH DIAGNOSTIC COMPONENTS", and copending U.S. Patent Application Serial No. 2005-0241387 by Miesel et al., entitled, "DIAGNOSTIC METHODS FOR BRANCHING CATHETER SYSTEMS" describe catheter integrity tests in further detail.

A pump motor stall test may be performed by driving a pump backwards (e.g., firing against the piston of the pump motor). A pump motor stall test may be used to determine if a problem with a therapeutic agent delivery system is due to a moving part within the pump or an issue with one or more of the catheters that deliver therapy from the pump to one or more target therapy delivery sites.

Integrity measurements are not limited to the examples described above. Integrity measurements may generally comprise measurements that test the functionality of any component of therapy system 10. For example, performing an integrity measurement may comprise running software, hardware, and/or firmware diagnostics to test the integrity of IMD 14. Other examples testing an array of capacitors used to store energy for the delivery of stimulation pulses, or testing a power source of the IMD.

After an integrity measurement is performed, remote networking device 4 may receive a result of the integrity measurement. For example, remote networking device 4 may receive status data 7 including a result of the integrity measurement. In some embodiments, IMD 14 or patient programmer 26 may perform a preliminary analysis based on the result of the integrity measurement. Based on the preliminary analysis, IMD 14 or patient programmer 26 may change a mode of operation of IMD 14 to address any issue identified. IMD 14 and/or patient programmer 26 may transmit status data indicating any change in the mode of operation of IMD 14 to remote networking device 4 along with the result of the integrity measurement.

In some embodiments, processor 6 of remote networking device 4 may analyze the result of the integrity measurement to identify problems with therapy system 10 and, upon identifying a problem, suggest a correction for the identified problem, e.g., to a user via U/I 8. In embodiments in which IMD 14 or patient programmer 26 performed a preliminary analysis, the analysis performed by processor 6 may be more extensive. If processor 6 identifies an issue with IMD 14, processor 6 may sent a command to IMD 14 via network 2 to change a mode of operation of IMD 14. For example, processor 6 may identify a dysfunctional electrical path and send a command to patient programmer 28 and/or IMD 14 to lock out the electrode(s) of the dysfunctional path to prevent the electrode(s) from being selected to deliver therapy. Processor 6 may analyze the result of the integrity measurement as the result is received. In other embodiments, the result may be stored as status data 7 within memory 5 of remote networking device 4 for analysis at a later time.

In other embodiments, remote networking device 4 may send a request to IMD 14 via network 2 to perform a more sophisticated integrity measurement based on the result of an initial integrity measurement. For example, remote networking device 4 may request an additional lead integrity test at a more accurate setting (e.g., a higher amplitude) or request that the integrity measurement be repeated to allow statistical analysis over time.

The analysis of status data 7 and the generation of requests and/or commands at remote networking device 4 may be performed by processor 6 of remote networking device 4, an authorized user of remote networking device 4, or any combination thereof. For example, memory 5 of remote networking device 4 may store instructions that processor 6 may execute based on status data 7. Remote networking device 4 may generate requests for integrity measurements, analyze status data 7, and generate commands to address issues with IMD 14 in a responsive and automatic manner.

In other embodiments, processor 6 may present data received from IMD 14 to an authorized user, such as a clinician, a technician, a manufacturer, or another trained practitioner, via U/I 8. Status data 8 may be reviewed by one or more authorized users and requests for integrity measurements and commands changing the mode of operation of IMD 14 may be sent to IMD 14 via network 2 based on input from one or more of these users. Also, in some embodiments, requests to perform integrity measurements may be sent to IMD 14 based on a schedule or as requested by an authorized user. Such requests need not be based on status data 8 received from IMD 14.

Remote networking device 4 comprises a computing device, such as clinician programmer 20, a desktop or laptop computer, workstation, PDA, or the like. In some embodiments, remote networking device 4 may comprise a plurality of networked devices, such as a server and a workstation. U/I may comprise a display and input media, such as a keyboard, keypad, or pointing device. As illustrated in FIG. 1, remote networking device 4 comprises a communication module 9 for communicating with network 2. Communication module 9 may comprise any known network interface, such as an Ethernet interface.

Processor 6 may comprise any one or more of a microprocessor, application specific integrated circuit (ASIC), digital signal processor (DSP), discrete logic circuitry, or the like. Memory 5 may comprise any fixed or removable, volatile or non-volatile medium, such as one or more of a random access memory (RAM), read-only memory (ROM), CD-ROM, hard disk, flash memory, or the like. Memory 5 may comprise program instructions that, when executed by processor 6, cause processor 6 and remote networking device 4 to provide the functionality described herein.

Remotely requesting an integrity measurement and receiving results of the measurement remotely may provide a patient and IMD access to a remotely-located clinician, manufacturer, and/or other authorized user without requiring a clinic visit. Additionally, a remotely located computing device may contain more processing power and memory and be more easily updated with new data processing algorithms than IMD 14 or patient programmer 26. Also, determining which integrity measurements to perform and analyzing data remotely may help prolong the battery life of IMD 14 and/or patient programmer 26.

Figure 2:
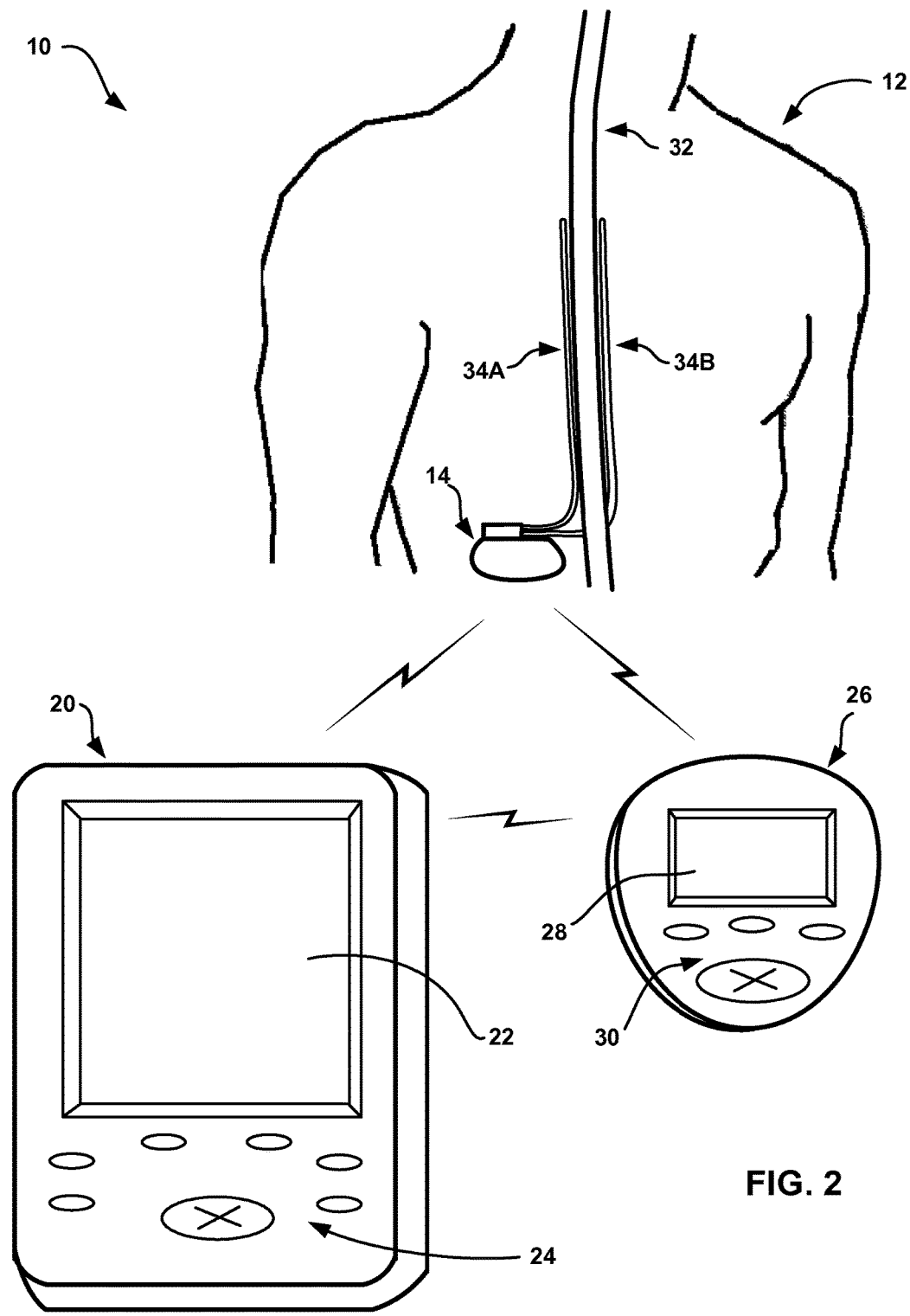
FIG. 2 is a conceptual diagram further illustrating some components of an example system in which integrity diagnostics may be remotely requested.

FIG. 2 is a conceptual diagram illustrating components of a system 10 in greater detail. In particular, FIG. 2 illustrates IMD 14, patient programmer 26, and clinician programmer 20 in greater detail. In the illustrated example, IMD 14 is coupled to therapy delivery elements 34A and 34B (collectively "therapy delivery elements 34"). In the example of FIG. 2, IMD 14 is implanted in the abdomen of patient 12. However, in other embodiments, IMD 14 may be external or subcutaneously implanted at another location in the body of a patient 12 (e.g., in a chest cavity, lower back, or buttocks of patient 12). In the illustrated embodiment, IMD 14 is coupled to two therapy delivery elements 28 to deliver therapy to two target therapy delivery sites. In other embodiments, IMD 14 may be coupled to a single therapy delivery element or more than two therapy delivery elements, e.g., to deliver therapy to more or fewer target therapy delivery sites.

In the embodiment of therapy system 10 shown in FIG. 2, the target therapy delivery sites are proximate to the spinal column 32. Accordingly, therapy delivery elements 28 may deliver therapy to, for example, spinal column 32 or surrounding tissue. Therapy delivery to the spinal column or surrounding tissue may help treat, for example, chronic pain or spinal cord injury. IMDs 14 according to the invention, however, may deliver a variety of therapies formulated for different disorders or symptoms, such as tremor, Parkinson's disease, multiple sclerosis, cerebral palsy, amyotrophic lateral sclerosis, dystonia, torticollis, epilepsy, pelvic floor disorders, gastroparesis, paralysis (e.g., functional electrical stimulation (FES) of muscles) obesity, pelvic floor disorders, urinary control disorders, fecal control disorders, interstitial cystitis, sexual dysfunction, and pelvic pain. Thus, in alternate embodiments, the target therapy delivery sites to which therapy delivery elements 28 extend may include or be proximate to any other nerve or tissue site in the body of patient 12. For example, target therapy delivery sites may include a pelvic nerve, pudendal nerve, stomach, bladder, or within a brain or other organ of patient 12, or within a muscle or muscle group of patient 12. System 10 may include any type of IMD for delivering therapy to patient 12, such as an electrical stimulator or a therapeutic agent delivery device.

Clinician programmer 20 may, as shown in FIG. 2, be a handheld computing device. Clinician programmer 20 comprises a user interface that may include a display 22, such as a LCD or LED display, to display information to a user. The user interface for clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using a peripheral pointing device, such as a stylus or mouse. Keypad 24 may take the form of an alphanumeric keypad or a reduced set of keys associated with particular functions. Display 22 may also present so-called soft keys for selection by the user.

Patient programmer 26, as shown in FIG. 2, may also be a handheld computing device. Patient programmer 26 includes a user interface which may comprise a display 28 and a keypad 30, to allow patient 12 to interact with patient programmer 26. In some embodiments, display 28 may be a touch screen display, and patient 12 may interact with patient programmer 26 via display 28. Patient 12 may also interact with patient programmer 26 using a peripheral pointing device, such as a stylus or mouse. As previously described, patient 12 may use patient programmer 26 to control the delivery of therapy by IMD 14, and patient programmer 26 may act as an intermediary for communication between IMD 14 and network 2.

Figure 3:
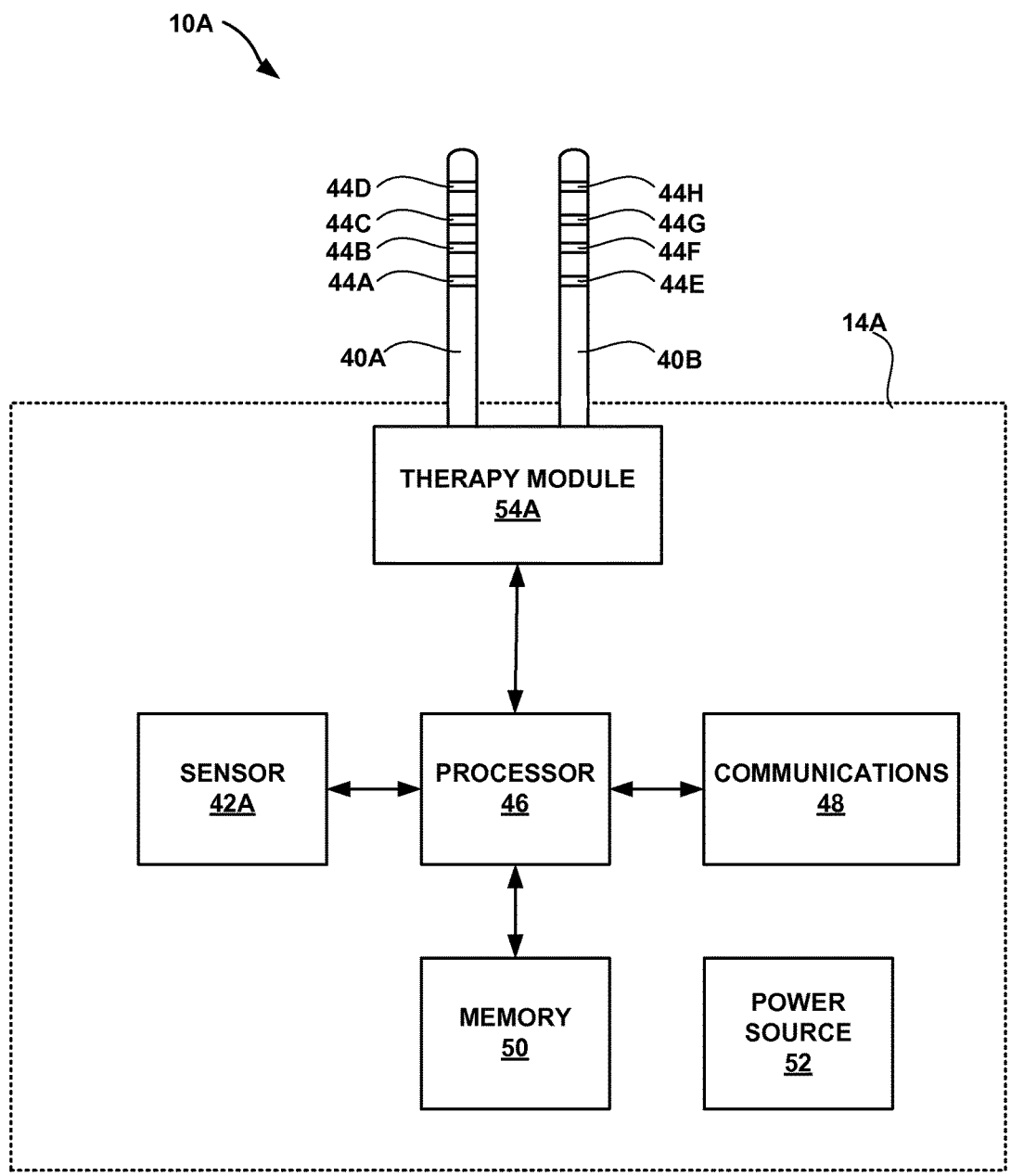
FIG. 3 is a functional block diagram further illustrating the implantable medical device of the system of FIG. 2.

FIG. 3 is a functional block diagram illustrating an example IMD 14A that takes the electrical stimulator. In the illustrated embodiment, IMD 14A includes a sensor 42, a processor 46, a communication module 48, memory 50, power supply 52, and therapy module 54A. Therapy module 54A is coupled to therapy delivery elements 40A and 40B (collectively "therapy delivery elements 40").

In the illustrated embodiment, therapy delivery elements 40 are leads including electrodes configured to deliver electrical stimulation to patient 12. Leads 40A and 40B respectively include electrodes 44A-44D and electrodes 44E-44H (collectively, "electrodes 44"). The configuration, type, and number of leads and electrodes illustrated in FIG. 3 are merely exemplary, and, in other embodiments, any other configuration, type, and/or number of electrodes may be used. Electrodes 44 may be ring electrodes or other types of electrodes such as cuff electrodes, paddle electrode leads, and electrodes formed on a housing of IMD 14A. In embodiments in which electrodes 44 are ring electrodes, electrodes 44 may be positioned at various positions along the length of leads 40, e.g., at a distal end, a proximal end, or medially located between the distal and proximal ends of leads 40.

Each of leads 40 may have multiple conductors, each corresponding to one or more of electrodes 44, to electrically connect electrodes 44 to IMD 14A. Leads 40 may be directly connected to IMD 14A, or may be connected to IMD 14A via one or more lead extensions. Conductors within a lead extension couple the conductors within a lead to IMD 14A. An electrode, the conductors that couple the electrode to IMD 14A, and tissue proximate to the electrode may be referred to as an electrical "path," through which IMD 14A may sense electrical activity within patient 12 and/or deliver stimulation to patient 12.

Therapy module 54A may include an implantable stimulation generator or other stimulation circuitry, e.g., capacitive elements and switches that delivers electrical signals to patient 12 via at least some of electrodes 44 under the control of processor 46. Processor 46 may control therapy module 54A to deliver stimulation therapy according to one or more selected programs. For example, processor 46 may control therapy module 54A to deliver electrical pulses with the amplitudes and widths, and at the rates specified by the one or more selected programs. Processor 46 may also control therapy module 54A to deliver the pulses via a selected subset of electrodes 44 with selected polarities, as specified by the selected programs. Processor 46 may include any one or more of a microprocessor, a controller, a digital signal processor (DSP), an application specific integrated circuit (ASIC), a field-programmable gate array (FPGA), discrete logic circuitry, or the like.

Memory 50 may store program instructions defining therapy programs that are available for therapy delivery via therapy module 54A. Memory 50 may also store status data 7 recorded by processor 46. As previously described in this disclosure, status data 7 may include data from one or more sensors, alerts from patient 12 and/or IMD 14A, results of an integrity measurement, or any other data relevant to the status and operation of the therapy delivery system. Memory 50 may also store program instructions that, when executed by processor 46, cause processor 46 and IMD 14A to provide the functionality ascribed to them herein. Memory 50 may include for example any volatile, non-volatile, magnetic, optical, or electrical media. For example, memory 50 may include any one or more of a random access memory (RAM), read-only memory (ROM), non-volatile RAM (NVRAM), electronically erasable programmable ROM (EEPROM), flash memory, or the like.

Communications module 48 includes circuitry for communication with clinician programmer 20, patient programmer 26, and/or remote networking device 4. Communications module 48 may include circuitry for wireless, RF communication according to any of a variety of local wireless communication standards, such as the Bluetooth standard, any of the IEEE 802.11 standards, or a proprietary medical device telemetry protocol. Communications module 48 may allow processor 46 to connect to network 2 to receive requests from remote networking device 4 and/or transmit status data 7 to remote networking device 4. Processor 46 may transmit status data 7 to remote networking device 4 via communications module 48 in response to receiving a request from remote networking device 4. Alternatively, processor 46 may automatically transmit status data 7 to remote networking device 4 via telemetry interface 48 in accordance with a schedule, on an opportunistic basis, or based on memory capacity.

As further shown in FIG. 3, system 10 may include one or more sensors that sense activity or physiological conditions within patient 12. Sensors may be, for example, activity, chemical, optical, temperature, pressure, and/or electrical sensors. Although the example of FIG. 3 includes sensor 42A within IMD 14A, sensors may in some embodiments be located outside of an IMD 14, and communicate data representing activity or a physiological condition to the IMD 14 by a wired connection, e.g., lead, or wireless telemetry, e.g., via communication module 48. Data from sensor 42A may be received by processor 46, and stored in memory 52. Sensor 42A may sense activity or physiological conditions pertinent to the control of therapy delivered by IMD 14A.

The activity and/or physiological conditions sensed by sensor 42A may be useful in identifying a state or phase of physiological activity, or a transition between different phases of activity. Processor 46 may use data received from sensor 42A to adjust therapy delivery. For example, processor 46 may use data received from sensor 42A to adjust therapy parameters such as voltage or current pulse amplitudes, pulse widths, pulse rates, electrode combinations, or polarities of selected electrodes. Processor 46 may adjust therapy delivery based on other data, such as user input or timing data, either individually or in combination with data received from sensor 42A.

The physiological parameter detected by sensor 42A may reflect the severity or prevalence of pain, movement disorders, epilepsy, mood disorders, cardiac disorders, gastrointestinal or urinary disorders, or side-effects associated with the treatment of such symptoms or disorders. Data from sensor 42A stored within memory 50 may include raw data derived from the signals output by the sensor, averages or other statistical representations of such data, or any other metric derived from such data.

The illustrated components of IMD 14A receive energy from a power source 52, which may be a battery or other suitable power source. Power source 52 may take the form of a small, rechargeable or non-rechargeable battery, or an inductive power interface that transcutaneously receives inductively coupled energy. In the case of a rechargeable battery, power source 52 similarly may include an inductive power interface for transcutaneous transfer of recharge power.

Memory 50 may store instructions that may be executed by processor 46 to perform integrity measurements. For example, remote networking device 4 may send a request to IMD 14A via network 2 which causes processor 46 to perform an integrity measurement according to instructions stored in memory 50. In other embodiments, instructions for performing the integrity measurement may be sent to IMD 14A via network 2. In some embodiments, memory 50 may store results of integrity measurements.

One example of a diagnostic integrity measurement that may be performed by processor 46 is a lead integrity test. A lead integrity test may comprise measuring the impedance of an electrical path including an electrode (e.g., one of electrodes 44), conductors that couple the electrode to IMD 14A, and tissue proximate to the electrode. Measuring the impedance of one or more electrical paths associated with leads 40 coupled to IMD 14A may aid in identifying dysfunctional electrical paths (e.g., paths that may be unable to provide adequate or reliable sensing or therapy due to, for example, degradation of the lead material, tissue growth proximate to an electrode, a short, or a fracture) among the paths provided by leads 40 coupled to IMD 14A. In general, integrity measurements performed by processor 46 may comprise measurements that test the functionality, accuracy, operating condition, or performance of any component of therapy system 10A. For example, performing an integrity measurement may comprise running software, hardware, and/or firmware diagnostics to test the integrity of IMD 14A.

Figure 4:
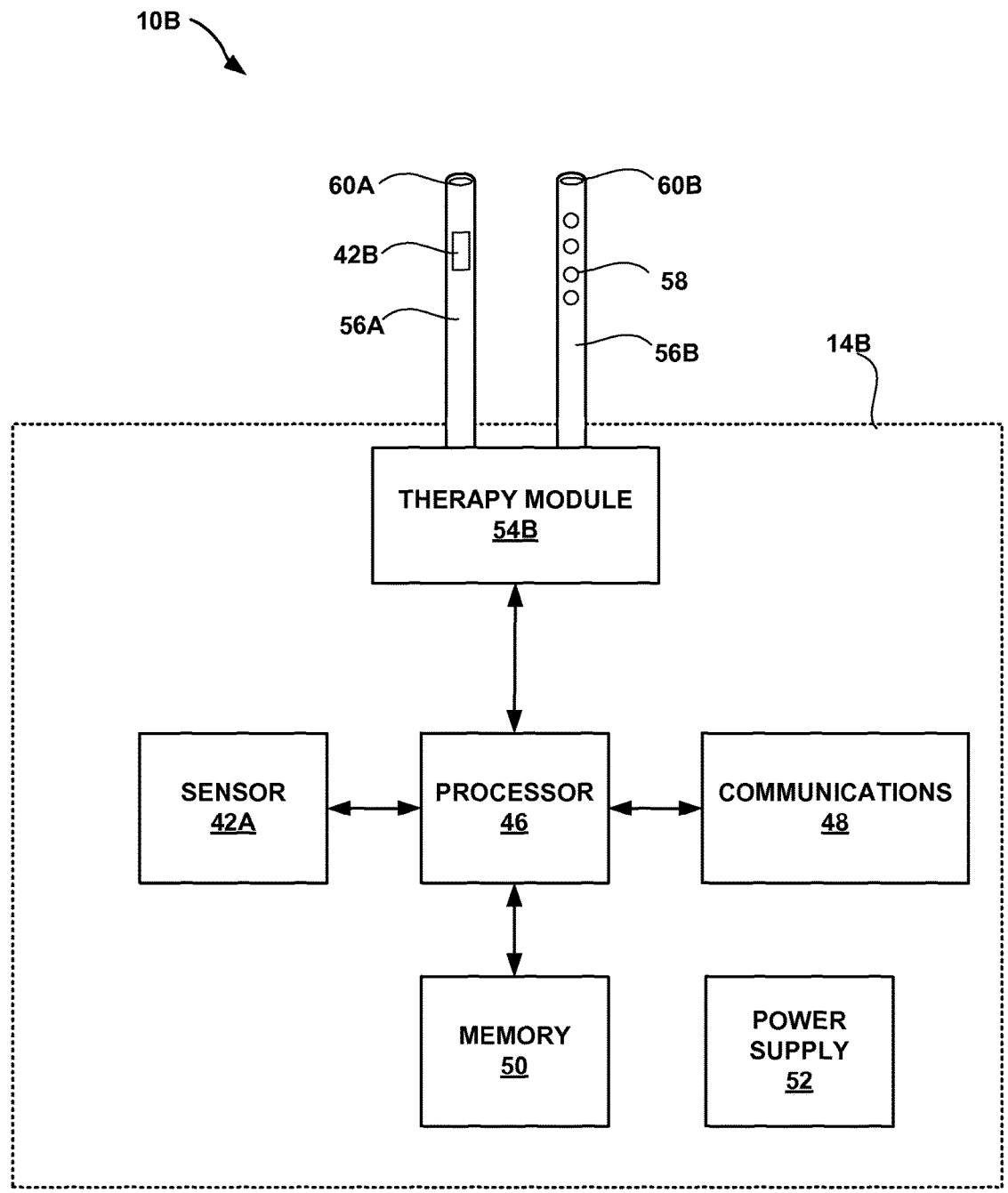
FIG. 4 is a functional block diagram illustrating another example implantable medical device which may receive requests to perform integrity diagnostics from a remote networking device.

FIG. 4 is a functional block diagram illustrating another IMD embodiment. In particular, FIG. 4 illustrates an IMD 14B that delivers a therapeutic agent to patient 12 via therapy delivery elements 56A and 56B (collectively "therapy delivery elements 56"). Therapy delivery elements 56 may also be referred to as therapeutic agent delivery elements or catheters. Similar to IMD 14A, IMD 14B includes sensor 42, processor 46, communications module 48, memory 50, power supply 52, and a therapy module 54B.

Each of catheters 56 may have an elongated tubular body with an inner lumen. With reference to FIG. 4, each elongated body may include a proximal opening to receive the therapeutic agent from IMD 14B and a distal outlet 60A, 60B (collectively, "outlets 60") for delivery of the therapeutic agent to one or more target therapy delivery sites. Additionally or alternatively, the elongated body may include one or more lateral outlets 58 formed in a lateral wall of the elongated body that provide fluid communication between the inner lumen and the outside of the elongated body. Outlets 58 may be positioned at various axial positions along the length of the elongated body, as well as various circumferential positions. Lateral outlets 58 may be concentrated towards a distal end of the catheter. The configuration, type, and number of outlets illustrated in FIG. 4 are merely exemplary, and, in other embodiments, any other configuration, type, and/or number of outlets may be used.

Therapy module 54B may include one or more therapeutic agent reservoirs and one or more pump units that pump the therapeutic agent from the fluid reservoirs through catheters 56 to the one or more target therapy delivery sites under the control of processor 46B. The fluid reservoirs may provide access for filling, e.g., by percutaneous injection of a therapeutic agent via a self-sealing injection port. Catheters 56 may, for example, deliver, i.e., infuse or disperse, a therapeutic agent from the fluid reservoirs to the same or different target therapy delivery sites within patient 12 under the control of processor 46. Processor 46 may control which therapeutic agents are delivered and the dosage of the therapeutic agents delivered to patient 12. For example, processor 46 may control therapy module 56B to delivery a therapy according to flow rates, agent types or concentrations, and infusion types, e.g., continuous or bolus, specified by the one or more selected programs. As described with respect to FIG. 3, processor 46 may include any one or more of a microprocessor, a controller, a digital signal processor (DSP), an application specific integrated circuit (ASIC), a field-programmable gate array (FPGA), discrete logic circuitry, or the like.

Although "therapeutic agent delivery device" and "therapeutic agent" is used for purposes of explanation, other substances may be delivered to patient 12. For example, IMD 14B may deliver saline solution, fluoroscopy agents, or disease diagnostic agents, which may or may not be intended to have a therapeutic effect, to patient 12. Any therapeutic, diagnostic, or other substance may be delivered using IMD 14B. In some embodiments, the substance delivered using IMD 14B may contain one or more drugs. The drugs will typically be fluids (e.g., liquids) or contained in fluid carriers (e.g., liquid carriers) as either solutions or mixtures.

Substances delivered using IMD 14B may be intended to have a therapeutic effect such as pharmaceutical compositions, genetic materials, biologics, and other substances. Pharmaceutical compositions are typically chemical formulations intended to have a therapeutic effect such as intrathecal antispasmodics, pain medications, chemotherapeutic agents, and the like. Pharmaceutical compositions may be configured to function in an implanted environment with characteristics such as stability at body temperature to retain therapeutic qualities, concentration to reduce the frequency of replenishment, and the like. Genetic materials include substances intended to have a direct or indirect genetic therapeutic effect such as genetic vectors, genetic regulator elements, genetic structural elements, DNA, and the like. Biologics include substances that are living matter or derived from living matter intended to have a therapeutic effect such as stem cells, platelets, hormones, biologically produced chemicals, and the like.

Memory 50 may store program instructions defining therapy programs that are available for therapy delivery via therapy module 54B. Memory 50 may also store status data 7 recorded by processor 46. As previously described in this disclosure, status data 7 may include data from one or more sensors, alerts from patient 12 and/or IMD 14, results of an integrity measurement, or any other information relevant to the status and operation of the therapy delivery system. As indicated above, memory 50 may include instructions that, when executed by processor 46, cause processor 46 and IMD 14B to provide the functionality described herein.

Like IMD 14A, IMD 14B includes a sensor 42A that senses activity or physiological conditions within patient 12. Additionally, a sensor 42B is coupled to IMD 14B via catheter 56A. Sensor 42B may sense, for example, flow or pressure within catheter 56A, and communicate sensed data to IMD 14B via a wired connection of wireless telemetry.

One example of an integrity measurement that may be performed by processor 46 in IMD 14B is a catheter integrity test. A catheter integrity test may comprise measuring a pressure differential in one of catheters 56, e.g., catheter 56A via sensor 42C. Such a measurement may aid to detecting flow issues within catheters 56. If functioning properly, for a given flow rate, the pressure within catheter 56 may be approximately equal to a normal, expected level. Deviations from the normal pressure may indicate failure of a catheter 56. In other embodiments, the flow of a therapeutic substance within a catheter 56 may be measured (e.g., via sensor 42C) to identify issues (e.g., occlusions, kinks, tears, and leaks) with the catheter.

Additionally or alternatively, a pump motor stall test may be performed on IMD 14B by driving a pump of therapy module 54B backwards (e.g., firing against the piston of the pump motor). A pump motor stall test may be used to determine if a problem with a therapeutic agent delivery by IMD 14B is due to a moving part within the pump or an issue with one or more of catheters 56 that deliver therapy from the pump to one or more target therapy delivery sites.

As another example, processor 46 may perform an integrity measurement by changing an operating parameter of the pump of therapy module 54B and monitoring how therapy system 10B is affected. For example, a pump stroke that differs substantially from the pump stroke used to deliver therapy may be used to aid in determining if therapy system 10B is functioning properly and, if applicable, what is causing therapy system 10B to function improperly. The pump stroke may be increased and the pulses may be distributed to maintain a similar average flow rate of therapeutic agent to patient 12. The manner in which pulses are delivered to patient 12 can be used to identify issues with therapy delivery system 10B and may potentially help address the issues identified. For example, if catheter 56B is partially occluded, a higher pulse stroke may aid in clearing the occlusion from catheter 56B.

Integrity measurements are not limited to the examples described above. In general, integrity measurements may comprise measurements that test the functionality of any component of therapy system 10B. For example, performing an integrity measurement may comprise running software, hardware, and/or firmware diagnostics to test the integrity of IMD 14.

Figure 5:
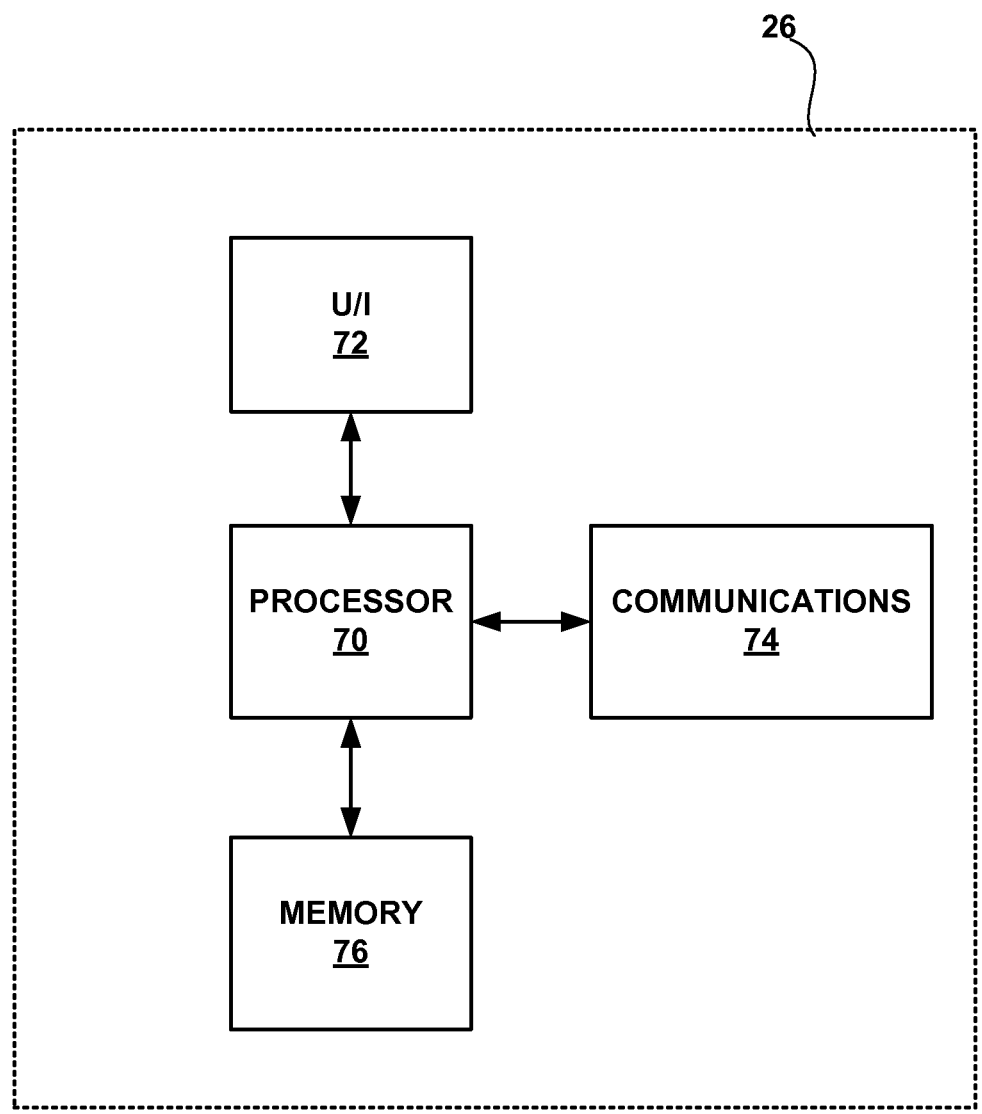
FIG. 5 is a functional block diagram illustrating components of patient programmer 26 according to one embodiment of the invention.

FIG. 5 is a functional block diagram illustrating components of patient programmer 26 according to one embodiment of the invention. As illustrated by FIG. 5, programmer 26 may include a processor 70, user interface (U/I) 72, communication module 74, and memory 76. A user, such as patient 12, may interact with processor 70 via U/I 52, which may include, for example, display 28 and keypad 30 (FIG. 2). Processor 70 may communicate with IMD 14, clinician programmer 20, and network 2 via communication module 74, which may include any RF or wired interface. Memory 76 may store status data 7 received from IMD 14. Memory 76 program instructions that, when executed by processor 70 cause processor 70 and programmer 26 to provide any of the functionality ascribed to them herein, such as acting as an intermediary between IMD 14 and remote networking device 4, providing an interface for communication by patient 12 with the remote networking device, collecting status data 7, analyzing status data 7, and the like.

Figure 6:
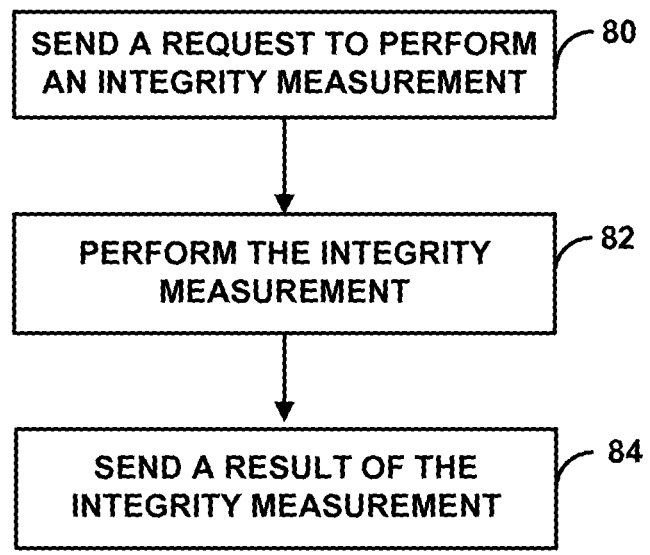
FIG. 6 is a flow diagram illustrating an example method of remotely requesting an integrity measurement.

FIG. 6 is a flow chart illustrating an example method of remotely requesting an integrity measurement. Remote networking device 4 may send a request to IMD 14 via network 2 to perform an integrity measurement, such as a lead integrity test on all electrodes, a lead integrity test on the electrodes currently being used to deliver therapy, a catheter integrity test, and/or a pump motor stall test (80). The request sent from remote networking device 4 to IMD 14 may be based on status data 7, a request from a clinician or other trained practitioner, or a schedule. IMD 14 performs the integrity measurement according to the request received via network 2 (82). In some embodiments, the request comprises instructions describing how to perform the integrity measurement. In other embodiments, the instruction may be stored within IMD 14, and the request sent from remote networking device 4 may prompt IMD 14 to access the instructions.

A result of the integrity measurement is sent from IMD 14 to remote networking device 4 via network 2 (84). Remote networking device 4, a clinician, or another trained practitioner may analyze the result of the integrity measurement to identify problems with therapy system 10. If a problem is identified, a correction may be sent to IMD 14 via network 2. For example, remote networking device 4 may identify a dysfunctional electrical path and send a request to patient programmer 26 and/or IMD 14 to lock out the electrode(s) of the dysfunctional path to prevent the electrode(s) from being selected to deliver therapy. Remote networking device 4 may also act to cause a follow-up visit, by notifying the patient or clinician, that would address the issue by surgical intervention or other means.

In other embodiments, remote networking device 4, the clinician, or the trained practitioner may require additional information from IMD 14 in order to identify potential issues. For example, based on the results of the initial integrity measurement, remote networking device 4 may send a request to IMD 14 via network 2 to perform a more sophisticated integrity measurement. Remote networking device 4 may, for example, request an additional lead integrity test at a more accurate setting (e.g., a higher amplitude) or request that the integrity measurement be repeated to allow statistical analysis over time.

Various embodiments of the invention have been described. These and other embodiments are within the scope of the following claims.

The invention claimed is:

1. A remote networking device comprising:
a communication module; and
a processor configured to send a request to perform an integrity measurement to an implantable medical device via the communication module and a network, receive a result of the integrity measurement from the implantable medical device via the network, analyze the result of the integrity measurement, and automatically send a command to the implantable medical device via the communication module and the network to change a mode of operation of the medical device based on the analysis of the result of the integrity measurement.

2. The remote networking device of claim 1, wherein the implantable medical device comprises a stimulator coupled to a lead including one or more electrodes, the integrity measurement comprises testing an electrical path from the medical device to at least one of the electrodes, and the command locks out at least one of the electrodes from being selected for delivery of therapy.

3. A method comprising:
sending a request from a remote networking device via a network to an implantable medical device to perform an integrity measurement;
receiving a result of the integrity measurement from the implantable medical device via the network;
analyzing, by the remote networking device, the result of the integrity measurement; and
automatically sending a command from the remote networking device to the implantable medical device via the network to change a mode of operation of the implantable medical device based on the analysis of the result of the integrity measurement.

4. The method of claim 3, wherein the implantable medical device comprises a stimulator coupled to a lead including one or more electrodes, and sending the request to perform the integrity measurement comprises sending a request to test an electrical path from the implantable medical device to at least one of the electrodes.

5. The method of claim 4, wherein the command comprises locking out at least one of the electrodes from being selected for delivery of therapy.

6. The method of claim 3, wherein the implantable medical device comprises a pump coupled to one or more catheters, and sending the request to perform the integrity measurement comprises sending a request to measure at least one of pressure or flow within a lumen of at least one of the catheters.

7. A system comprising:
an implantable medical device; and
a remote networking device configured to send a request to perform an integrity measurement to the implantable medical device via a network,
wherein the implantable medical device performs the integrity measurement and sends a result of the integrity measurement to the remote networking device via the network,
wherein the remote networking device analyzes the result of the integrity measurement, and automatically sends a command to the implantable medical device via the network to change a mode of operation of the implantable medical device based on the analysis of the result of the integrity measurement.

8. A method comprising:
receiving a request to perform an integrity measurement at an implantable medical device from a remote networking device via a network, wherein the implantable medical device comprises at least one of a pump or a stimulator;
performing the integrity measurement at the implantable medical device of at least one component within or coupled to the implantable medical device in response to the request;
sending a result of the integrity measurement from the implantable medical device to the remote networking device via the network; and
receiving a command at the implantable medical device from the remote networking device via the network in response to the result of the integrity measurement, the command locking out the at least one component from being selected for delivery of therapy.

9. The method of claim 8, further comprising changing a mode of operation of the implantable medical device based on the result of the integrity measurement.

10. The method of claim 9, wherein changing the mode of operation comprises receiving a second command from the remote networking device via the network at the implantable medical device to change the mode of operation.

11. The method of claim 8, wherein the implantable medical device comprises the stimulator coupled to a lead including one or more electrodes, and performing the integrity measurement comprises testing an electrical path from the implantable medical device to at least one of the electrodes.

12. The method of claim 8, wherein the implantable medical device comprises the pump coupled to one or more catheters, and performing the integrity measurement comprises measuring at least one of pressure or flow within a lumen of at least one of the catheters.

13. The method of claim 8, wherein performing the integrity measurement comprises performing at least one of software, hardware, or firmware diagnostics.

14. The method of claim 8, wherein the at least one component comprises at least one electrode coupled to the at least one stimulator.

15. The method of claim 8, where receiving the request and sending the result via the network comprises receiving and sending the result via the Internet.

16. An implantable medical device comprising:
at least one of a pump or a stimulator,
a communication module; and
a processor configured to receive, from a remote networking device via a network and the communication module, a request to perform an integrity measurement of at least one component within or coupled to the implantable medical device,
wherein, upon receiving the request, the processor is configured to perform the integrity measurement and sends a result of the integrity measurement device to the remote networking device via the network and the communication module,
wherein the processor is configured to receive a command from the remote networking device in response to the result of the integrity measurement via the network and the communication module locking out the at least one component from being selected for delivery of therapy.

17. The implantable medical device of claim 16, wherein the processor is configured to change a mode of operation of the implantable medical device based on the result of the integrity measurement.

18. The implantable medical device of claim 17, wherein the processor is configured to receive a second command from the remote networking device via the network and the communication module to change the mode of operation.

19. The implantable medical device of claim 16, wherein the implantable medical device comprises the stimulator coupled to a lead including one or more electrodes, and the processor is configured to perform the integrity measurement by testing an electrical path from the implantable medical device to at least one of the electrodes.

20. The implantable medical device of claim 16, wherein the implantable medical device comprises the pump coupled to one or more catheters, and the processor is configured to perform the integrity measurement by measuring at least one of pressure or flow within a lumen of at least one of the catheters.

21. The implantable medical device of claim 16, wherein the processor is configured to perform the integrity measurement by performing at least one of software, hardware, or firmware diagnostics.

22. The implantable medical device of claim 16, wherein the at least one component comprises at least one electrode coupled to the at least one stimulator.

* * * * *